United States Patent
Cortes et al.

(10) Patent No.: US 11,584,716 B2
(45) Date of Patent: Feb. 21, 2023

(54) PRODUCTION OF ARYLPYRROL COMPOUNDS IN THE PRESENCE OF DIPEA BASE

(71) Applicant: BASF Agro B.V., Arnhem (NL)

(72) Inventors: David A. Cortes, Palmyra, MO (US); Ryan Michael Phillips, Palmyra, MO (US)

(73) Assignee: BASF AGRO B.V., Arnhem (NL)

( * ) Notice: Subject to any disclaimer, the term of this patent is extended or adjusted under 35 U.S.C. 154(b) by 168 days.

(21) Appl. No.: 16/492,119

(22) PCT Filed: Mar. 5, 2018

(86) PCT No.: PCT/EP2018/055261
§ 371 (c)(1),
(2) Date: Sep. 7, 2019

(87) PCT Pub. No.: WO2018/166819
PCT Pub. Date: Sep. 20, 2018

(65) Prior Publication Data
US 2021/0139422 A1    May 13, 2021

(30) Foreign Application Priority Data

Mar. 13, 2017 (EP) .................... 17160466

(51) Int. Cl.
*C07D 207/34* (2006.01)
*C07D 207/337* (2006.01)

(52) U.S. Cl.
CPC ....... *C07D 207/34* (2013.01); *C07D 207/337* (2013.01)

(58) Field of Classification Search
None
See application file for complete search history.

(56) References Cited

U.S. PATENT DOCUMENTS 4,929,634 A * 5/1990 Herman ............... C07D 207/42
514/426
5,030,735 A    7/1991 Addor et al.
(Continued)

FOREIGN PATENT DOCUMENTS

| EP | 0771787 A1 | 5/1997 |
| EP | 0821876 A1 | 2/1998 |
| WO | 03024222 A1 | 3/2003 |

OTHER PUBLICATIONS

International Search Report and Written Opinion for International Application No. PCT/EP2018/055261, dated May 16, 2018, 9 pages.

(Continued)

*Primary Examiner* — Craig D Ricci

(74) *Attorney, Agent, or Firm* — Marshall, Gerstein & Borun LLP

(57) ABSTRACT

A process A for the production of compounds of formula I is provided.

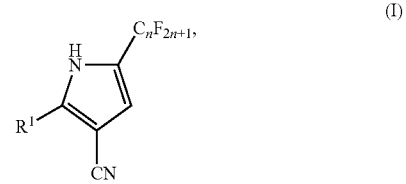

Process A includes Step A of reacting compounds of formula II

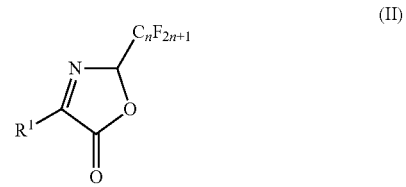

with 2,3-dihalopropionitrile or 2-haloacrylonitrile in the presence of DIPEA. A process B for the production of compounds of formula III is also provided.

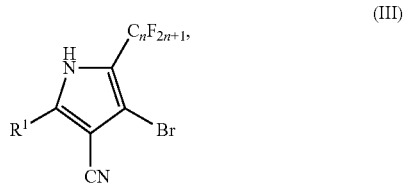

Process B includes Step B of reacting compounds of formula I with $Br_2$ in the presence of DIPEA. A process C for the production of compounds of formula IV is further provided.

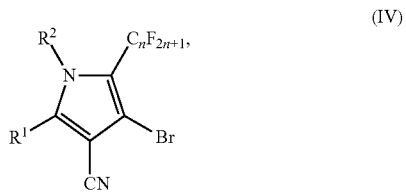

Process C includes Step C of reacting compounds of formula III with di($C_1$-$C_4$-alkoxy)methane and either $POCl_3$, or a mixture comprising $POCl_3$ and DMF, in the presence of DIPEA. Additionally, the use of DIPEA as a base in the (Continued)

production of compounds of formula I, compounds of formula III, or compounds of formula IV is provided.

14 Claims, 3 Drawing Sheets

(56) References Cited

U.S. PATENT DOCUMENTS

| | | |
|---|---|---|
| 5,118,816 A | 6/1992 | Doehner et al. |
| 5,144,041 A | 9/1992 | Doehner |
| 5,359,090 A * | 10/1994 | Doehner ............ C07D 207/325 548/561 |
| 5,446,170 A | 8/1995 | Kameswaran |
| 5,453,508 A | 9/1995 | Knapp |
| 5,679,826 A | 10/1997 | Mais et al. |

OTHER PUBLICATIONS

European Search Report for EP Patent Application No. 17160466.3, dated May 12, 2017, 4 pages.
Yokota, et al., "A novel synthesis of α-d-acrylonitrile ", Journal of Polymer Science: Polymer Chemistry Edition, vol. 18, Issue 5, May 1980, pp. 1609-1610.

* cited by examiner

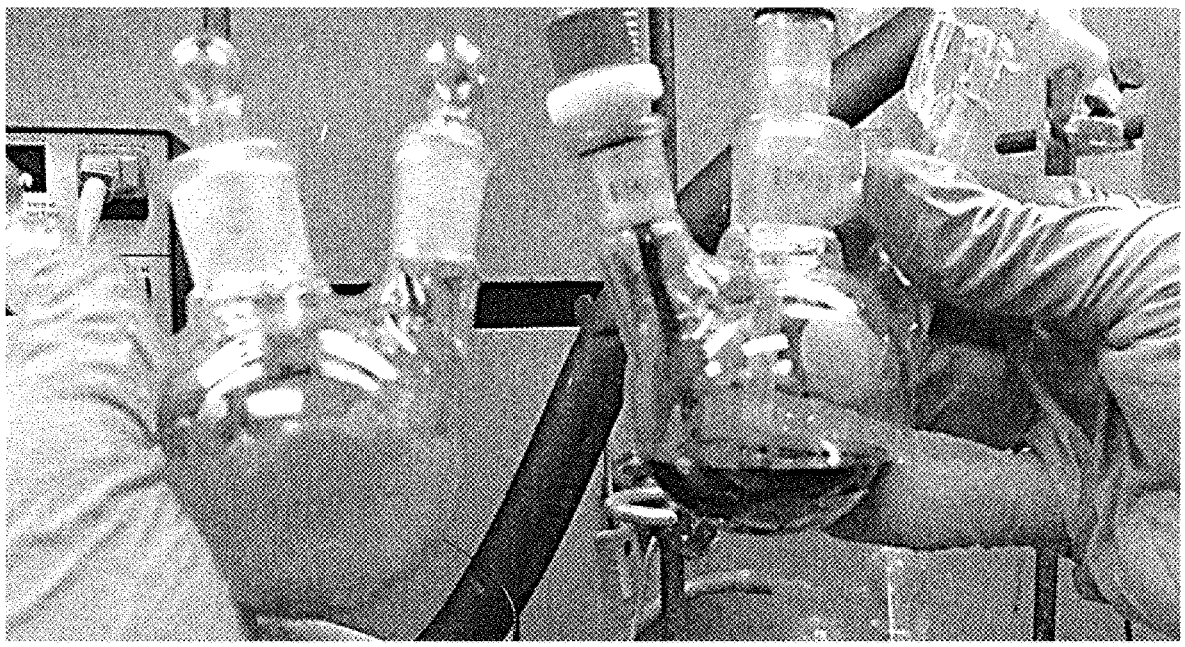

Figure 1: Slurry in left flask is reaction composition of Step A using TEA as a base. Clear solution in right flask is reaction composition of Step A using DIPEA as a base.

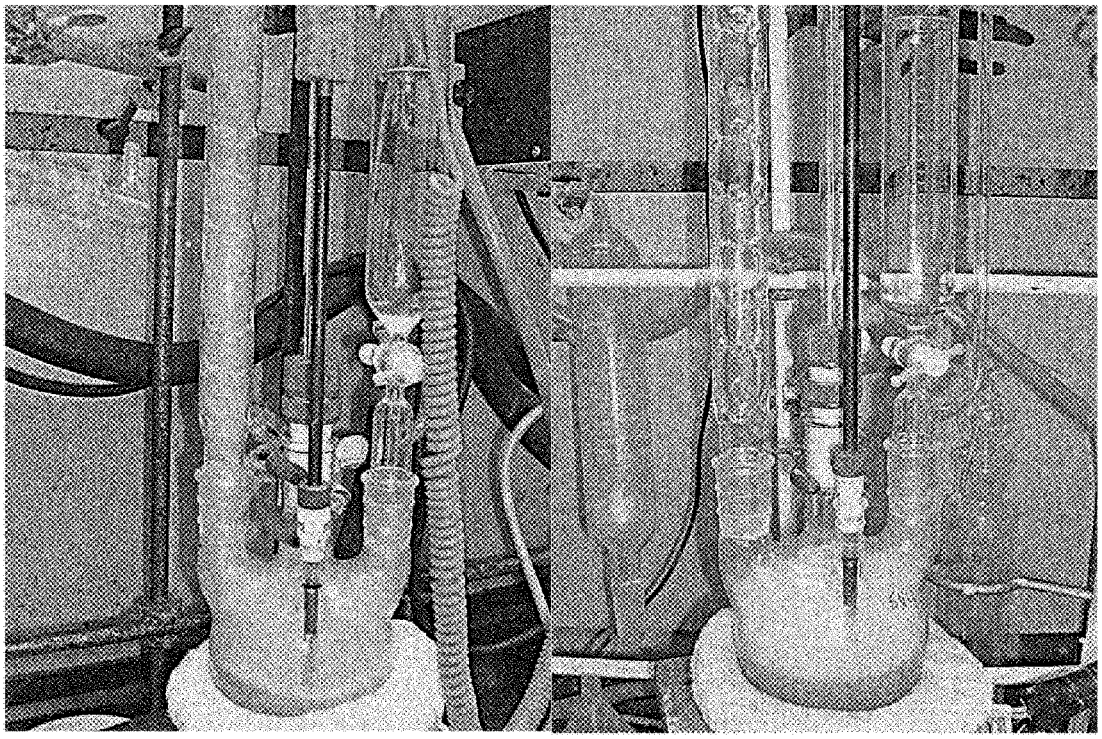

Figure 2: composition during the reaction of Step A using TEA (left) or DIPEA (right) as a base. Fog production in left set-up is so pronounced that it completely filly up the condenser, whereas the application of DIPEA reduces fog production considerably.

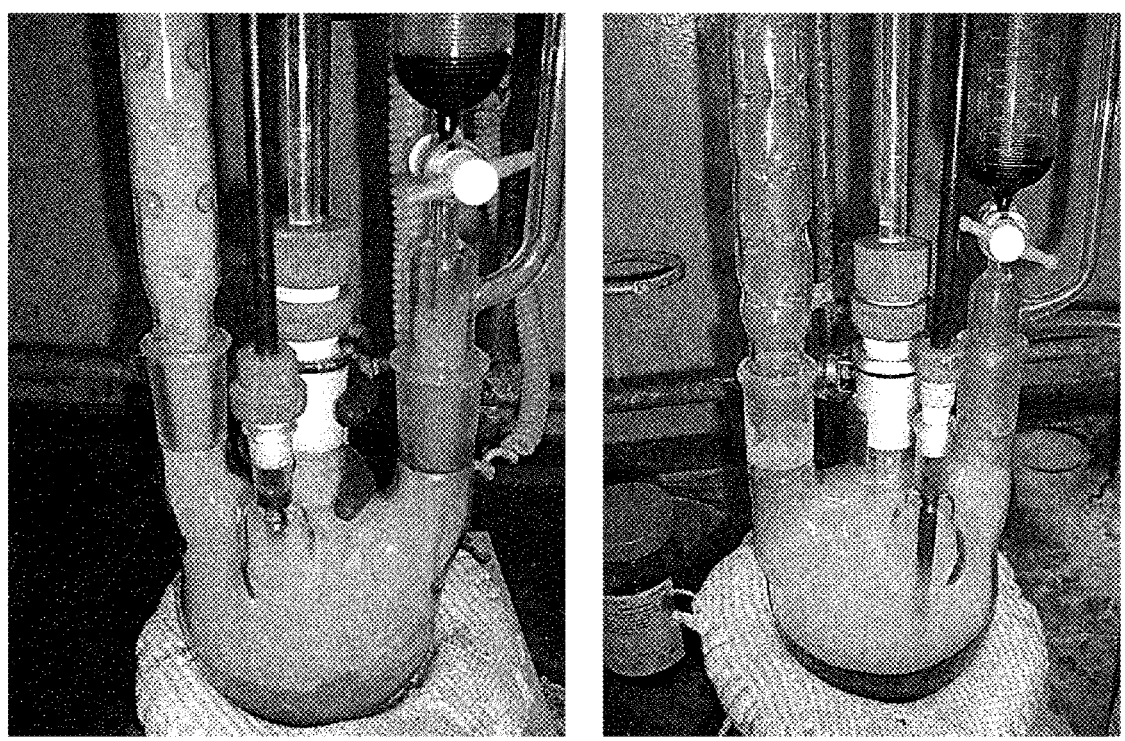
Figure 3: composition during the reaction of Step B using TEA (left) or DIPEA (right) as a base. Fog production in left set-up is so pronounced that it completely fills up the condenser, whereas the application of DIPEA reduces fog production considerably.
Figure 4: Reaction transfer of the composition of Step C using TEA as a base.

Figure 5: Reaction transfer of the composition of Process C using DIPEA as a base.

PRODUCTION OF ARYLPYRROL COMPOUNDS IN THE PRESENCE OF DIPEA BASE

CROSS-REFERENCE TO RELATED APPLICATIONS

This application is a U.S. National Phase Application of PCT/EP2018/055261, filed Mar. 5, 2018, which claims the benefit of priority to EP Application No. 17160466.3, filed Mar. 13, 2017, the contents of which are hereby expressly incorporated by reference in their entirety.

The invention relates to Process A for the production of compounds of formula I

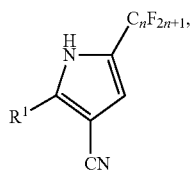

(I)

wherein the variables have the meaning
$R^1$ phenyl, substituted with none, one, or more, same, or different $R^{11}$;
$R^{11}$ F, Cl, Br, I, CN, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkyl-C(O)O, $C_1$-$C_4$-haloalkyl-C(O)O; or two substituents $R^{11}$ situated at adjacent phenyl ring-atoms together are a group —$OCH_2O$—, —$OCF_2O$—, or —CH═CH—CH═CH—, and form, together with the carbon atoms to which they are attached a 5- or 6-membered ring;
n 1, 2, or 3;
comprising Step A of reacting compounds of formula II

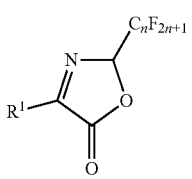

(II)

wherein the variables have the same meaning as defined for compounds of formula I; with 2,3-dihalopropionitrile (DHPN) or 2-haloacrylonitrile (HACN) in the presence of diisopropylethylamine (DIPEA).

The invention also relates to Process B for the production of compounds of formula III

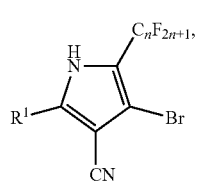

(III)

wherein the variables have a meaning as defined for compounds of formula I;

comprising Step B of reacting compounds of formula I with $Br_2$ (bromine) in the presence of DIPEA.

It also relates to Process C for the production of compounds of formula IV

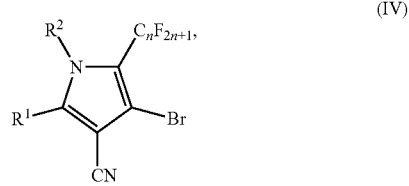

(IV)

wherein $R^1$ and n are as defined for compounds of formula I, and wherein $R^2$ is $C_1$-$C_4$-alkoxymethyl;

comprising Step C of reacting compounds of formula III with di($C_1$-$C_4$-alkoxy)methane and either $POCl_3$, or a mixture comprising $POCl_3$ and DMF (Vilsmeier reagent), in the presence of DIPEA.

The invention also relates to the use of DIPEA as a base in the production of compounds of formula I, compounds of formula III, or compounds of formula IV; to the use of DIPEA as a base in Step A; to the use of DIPEA as a base in Step B, and to the use of DIPEA as a base in Step C. Combinations of embodiments with other embodiments, regardless of their respective level of preference, are within the scope of the invention.

FIG. 1: pictures of reaction vessels in Step A reaction using TEA or DIPEA as base.

FIG. 2: pictures of reaction set-up in Step A reaction using TEA or DIPEA as base.

FIG. 3: picture or reaction set-up in Step B reaction using TEA or DIPEA as base.

FIG. 4: picture of the reaction mixtures in Step C reaction using TEA as a base.

FIG. 5: pictures of the reaction mixtures in Step C reaction using DIPEA as a base.

Pesticidal compounds of formulae III and IV and their production are known from U.S. Pat. Nos. 5,359,090, 5,144, 041, EP0821876A1, U.S. Pat. Nos. 5,453,508, 5,118,816, 5,446,170, and 5,030,735. Economically important insecticides chlorfenapyr and tralopyril fall within the definition of compounds of formulae III and IV, respectively. Due to the industrial and agricultural importance of these compounds, improved production processes of compounds of formulae III and/or IV, as well as of intermediate compounds of formula I, with higher yields, lower costs, fewer steps, and less waste material are desirable.

The production of compounds of formulae III and/or IV may be achieved by the following reaction sequence:

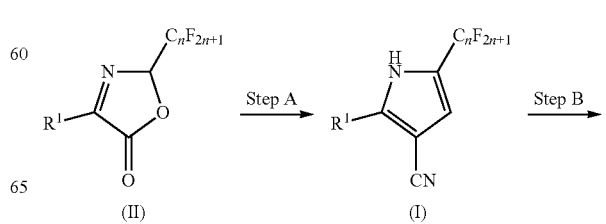

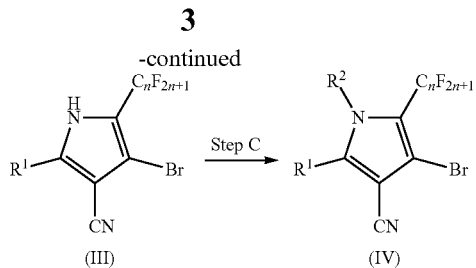

(III) → Step C → (IV)

Prior art teaches the use of triethylamine (TEA) as a base in the production processes of compounds of formulae III and/or IV. It has now surprisingly been found that the use of DIPEA as a base in steps A, B, and/or C, leads to a higher yield of compounds of formulae I, III and/or IV. The production process is simplified because less fog is produced in steps A, B, and C, which causes constrictions in the condensers of reactor facilities over time. The reaction mixtures are not slurries, but solutions, which facilitates the work-up process. The reactors do not need to be flushed with water to recover all precipitate, which avoids corrosive processes and saves costs. In particular, flushing glass reactors after steps B or C with water leads to glass corrosion, which can be avoided by the inventive process. Another advantage is an easy recovery of the base DIPEA after work-up of compounds of formulae I, III or IV. The base can be recovered in few steps, with low residual water-content, and at a high yield.

Compounds of formula I are produced in Process A comprising Step A of reacting compounds of formula II with DHPN or HACN in the presence of DIPEA.

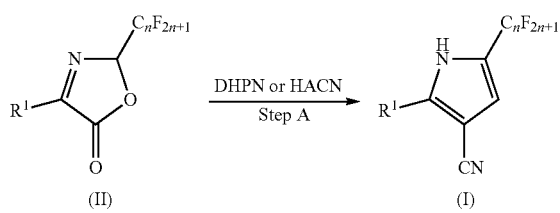

(II) → DHPN or HACN, Step A → (I)

wherein the variables have a meaning as defined for compounds of formula I.

Step A is usually carried out at temperatures of from 10° C. to 70° C., preferably from 15° C. to 60° C., in an inert solvent. Typically, Step C is carried out in the presence of DIPEA as the only base and no other additional bases are present, in particular not triethylamine. Preferably, the ratio of DIPEA to other bases in Step C is at least than 5:1, preferably at least 10:1, and in particular at least 100:1.

In one embodiment, Process A comprises the step of reacting compounds of formula II with DHPN. In another embodiment, Process A comprises the step of reacting compounds of formula II with HACN.

Suitable inert solvents are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, preferably $C_1$-$C_6$-cycloalkyl ethers, $C_1$-$C_6$-alkyl-$C_1$-$C_6$-alkyl ethers, $C_1$-$C_6$-alkyl-$C_3$-$C_6$-cycloalkyl ethers, $C_1$-$C_6$-polyol-$C_1$-$C_6$-alky ethers, and $C_1$-$C_6$-alkyl-$C_6$-$C_{10}$-aryl ethers, such as $CH_3CH_2OCH_2CH_3$, $(CH_3)_2CHOCH(CH_3)_2$, $CH_3OC(CH_3)_3$ (MTBE), $CH_3OCH_3$ (DME), $CH_3OCH_2CH_2OCH_3$, $CH_3OC(CH_3)_2CH_2CH_3$, dioxane, anisole, 2-methyltetrahydrofuran, tetrahydrofuran (THF), and diethylene glycol; esters, preferably esters of aliphatic $C_1$-$C_6$-alcohols with aliphatic $C_1$-$C_6$-carboxylic acids, esters of aromatic $C_6$-$C_{10}$-alcohols with aromatic $C_6$-$C_{10}$-carboxylic acids, cyclic esters of ω-hydroxy-$C_1$-$C_6$-carboxylic acids, such as $CH_3C(O)OCH_2CH_3$, $CH_3C(O)OCH_3$, $CH_3C(O)OCH_2CH_2CH_2CH_3$, $CH_3C(O)OCH(CH_3)CH_2CH_3$, $CH_3C(O)OC(CH_3)$, $CH_3CH_2CH_2C(O)OCH_2CH_3$, $CH_3CH(OH)C(O)OCH_2CH_3$, $CH_3CH(OH)C(O)OCH_3$, $CH_3C(O)OCH_2CH(CH_3)_2$, $CH_3C(O)OCH(CH_3)_2$, $CH_3CH_2C(O)OCH_3$, benzyl benzoate, and γ-butyrolactone; carbonates, such as ethylene carbonate, propylene carbonate, $CH_3CH_2OC(O)OCH_2CH_3$, and $CH_3OC(O)OCH_3$; nitriles, preferably $C_1$-$C_6$-nitriles, such as acetonitrile (ACN), and $CH_3CH_2CN$; ketones, preferably $C_1$-$C_6$-alkyl-$C_1$-$C_6$-alkyl ketones, such as $CH_3C(O)CH_3$, $CH_3C(O)CH_2CH_3$, $CH_3CH_2C(O)CH_2CH_3$, and $CH_3C(O)C(CH_3)_3$ (MTBK); amides and urea derivatives, preferably dimethylformamide (DMF), N-methyl-2-pyrrolidone (NMP), dimethyl acetamide (DMA), 1,3-dimethyl-2-imidazolidinone (DMI), 1,3-dimethyl-3,4,5,6-tetrahydro-2(1H)-pyrimidinone (DMPU), hexamethylphosphamide (HMPA); moreover dimethyl sulfoxide (DMSO), and sulfolane. Mixtures of the above solvents are also possible.

In one embodiment, the inert solvent comprises aliphatic hydrocarbons, aromatic hydrocarbons, nitriles, amides, or a mixture thereof. In another embodiment, the inert solvent comprises aliphatic $C_5$-$C_{16}$-hydrocarbons, aromatic $C_6$-$C_{10}$-hydrocarbons, $C_1$-$C_6$-nitriles, amides, or a mixture thereof. In another embodiment, the inert solvent comprises aromatic $C_6$-$C_{10}$-hydrocarbons, $C_1$-$C_6$-nitriles, DMF, or a mixture thereof. In another embodiment, the inert solvent comprises benzene, toluene, xylene, ACN, DMF, or a mixture thereof. In another embodiment, the inert solvent comprises a mixture of toluene, ACN, and DMF. In another embodiment, the inert solvent comprises ACN. In another embodiment, the inert solvent comprises a mixture of toluene and ACN. In another embodiment, the inert solvent comprises a mixture of toluene and DMF.

Suitable inert solvents usually comprise a polar aprotic solvent. In one embodiment, the inert solvent is a mixture of a one polar aprotic solvent and at a one non-polar solvent. In another embodiment, the inert solvent only consists of non-polar solvents.

Examples of polar aprotic solvents are esters, ketones, nitriles, amides and urea derivatives, DMSO, and sulfolane. Examples of non-polar solvents are aliphatic hydrocarbons, aromatic hydrocarbons, and ethers.

In case the solvent comprises a polar aprotic solvent, the concentration of the sum of all polar aprotic solvents with regard to the total amount of solvent is at least 20 wt %, preferably at least 30 wt %, more preferably at least 40 wt %, most preferably at least 60 wt %, and in particular at least 70 wt %. The sum of all polar aprotic solvents with regard to the total amount of solvent may be from 10 to 99 wt %, preferably from 20 to 95 wt %, more preferably from 25 to 90 wt %, most preferably from 50 to 80 wt %. In one embodiment, the solvent comprises at least 40 wt %, preferably at least 50 wt % of ACN with regard to the total amount of solvent.

The molar ratio of DIPEA to compounds of formula II is usually from 10:1 to 1:1, preferably from 5:1 to 1:1, more preferably from 4:1 to 1:1, most preferably from 3.5:1 to 2:1.

The molar ratio of DI PEA to compounds of formula II may be at least 1.5:1, more preferably at least 3:1. The molar ratio of compounds of formula II to either DH PN or H ACN may be from 1:1 to 1:5, most preferably from 1:1 to 1:3, and in particular from 1:1 to 1:2.

The concentration of compounds of formula II at the beginning of the reaction with regard to the total amount of solvent may be from 1 to 90 wt %, preferably 10 to 80 wt %, more preferably from 10 to 60 wt %, most preferably from 10 to 50 wt %, and in particular 15 to 20 wt %.

Compounds of formula II and either DHPN or HACN are typically mixed before DIPEA is added. The addition of DI PEA is usually carried out over a period of from 5 min to 120 min, preferably over a period of from 10 min to 60 min. After the addition of DIPEA has been initiated, the reaction usually takes from 15 minutes to 300 minutes, preferably 50 minutes to 150 minutes.

Typically, 2,3-dihalopropionitrile (DHPN) refers to 2,3-dichloropropionitrile; and 2-haloacrylnitrile (HACN) refers to 2-chloroacrylnitrile. DHPN and HACN compounds are commercially available. DHPN and HACN may alternatively be prepared as described in EP0771787 or Yokota et al., Journal of Polymer Science, Polymer Chemistry Edition, 1980, vol. 18(5), pp. 1609-10. Preferably, DHPN refers to 2,3-dibromopropionitrile. Preferably, HACN refers to 2-bromoacrylnitrile.

Compounds of formula III are produced in Process B comprising the reaction of compounds of formula I with $Br_2$ (bromine) in the presence of DIPEA

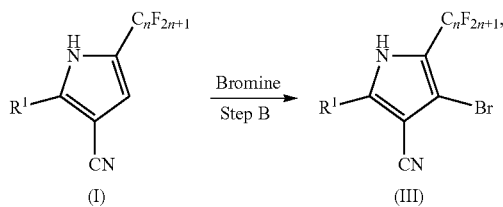

wherein the variables have a meaning as defined for compounds of formula I.

Step B is usually carried out at temperatures of from 20° C. to 60° C., preferably from 25° C. to 45° C., in an inert solvent and optionally in the presence of a catalyst. Typically, Step C is carried out in the presence of DIPEA as the only base and no other additional bases are present, in particular not triethylamine. Preferably, the ratio of DIPEA to other bases in Step C is at least than 5:1, preferably at least 10:1, and in particular at least 100:1.

Suitable inert solvents are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, preferably $C_1$-$C_6$-cycloalkyl ethers, $C_1$-$C_6$-alkyl-$C_1$-$C_6$-alkyl ethers, $C_1$-$C_6$-alkyl-$C_3$-$C_6$-cycloalkyl ethers, $C_1$-$C_6$-polyol-$C_1$-$C_6$-alky ethers, and $C_1$-$C_6$-alkyl-$C_6$-$C_{10}$-aryl ethers, such as $CH_3CH_2OCH_2CH_3$, $(CH_3)_2CHOCH(CH_3)_2$, $CH_3OC(CH_3)_3$ (MTBE), $CH_3OCH_3$ (DME), $CH_3OCH_2CH_2OCH_3$, $CH_3OC(CH_3)_2CH_2CH_3$, dioxane, and diethylene glycol; esters, preferably esters of aliphatic $C_1$-$C_6$-alcohols with aliphatic $C_1$-$C_6$-carboxylic acids, esters of aromatic $C_6$-$C_{10}$-alcohols with aromatic $C_6$-$C_{10}$-carboxylic acids, cyclic esters of ω-hydroxy-$C_1$-$C_6$-carboxylic acids, such as $CH_3C(O)OCH_2CH_3$, $CH_3C(O)OCH_3$, $CH_3C(O)OCH_2CH_2CH_3$, $CH_3C(O)OCH(CH_3)CH_2CH_3$, $CH_3C(O)OC(CH_3)_3$, $CH_3CH_2CH_2C(O)OCH_2CH_3$, $CH_3CH(OH)C(O)OCH_2CH_3$, $CH_3CH(OH)C(O)OCH_3$, $CH_3C(O)OCH_2CH(CH_3)_2$, $CH_3C(O)OCH(CH_3)_2$, $CH_3CH_2C(O)OCH_3$, benzyl benzoate, and γ-butyrolactone; carbonates, such as ethylene carbonate, propylene carbonate, $CH_3CH_2OC(O)OCH_2CH_3$, and $CH_{3O}C(O)OCH_3$; nitriles, preferably $C_1$-$C_6$-nitriles, such as ACN, and $CH_3CH_2CN$; alcohols, preferably $C_1$-$C_4$-alcohols and $C_2$-$C_4$-alkane diols, such as $CH_3OH$, $CH_3CH_2OH$, $CH_3CH_2CH_2OH$, $CH_3CH(OH)CH_3$, $CH_3(CH_2)_3OH$, and $C(CH_3)_3OH$, $CH_2(OH)CH_2(OH)$, $CH_3CH(OH)CH_2OH$; amides and urea derivatives, preferably DMF, NMP, DMA, DMI, DMPU, HMPA; moreover DMSO, and sulfolane. Mixtures of the above solvents are also possible.

In one embodiment, the inert solvent comprises aliphatic hydrocarbons, aromatic hydrocarbons, nitriles, amides, or a mixture thereof. In another embodiment, the inert solvent comprises aliphatic $C_5$-$C_{16}$-hydrocarbons, aromatic $C_6$-$C_{10}$-hydrocarbons, $C_1$-$C_6$-nitriles, amides, or a mixture thereof. In another embodiment, the inert solvent comprises aromatic $C_6$-$C_{10}$-hydrocarbons, $C_1$-$C_6$-nitriles, DMF, or a mixture thereof. In another embodiment, the inert solvents comprise benzene, toluene, xylene, ACN, DMF, or a mixture thereof. In another embodiment, the inert solvents comprise a mixture of toluene, ACN, and DMF. In another embodiment, the inert solvent comprises ACN. In another embodiment, the inert solvent comprises a mixture of toluene and ACN. In another embodiment, the inert solvent comprises a mixture of toluene and DMF.

In case the solvent comprises is a polar aprotic solvent, the concentration of the sum of all polar aprotic solvents with regard to the total amount of solvent is at least 20 wt %, preferably at least 30 wt %, more preferably at least 40 wt %, most preferably at least 60 wt %, and in particular at least 70 wt %. The sum of all polar aprotic solvents with regard to the total amount of solvent may be from 10 to 99 wt %, preferably from 20 to 95 wt %, more preferably from 25 to 90 wt %, most preferably from 50 to 80 wt %. In one embodiment, the solvent comprises at least 40 wt %, preferably at least 50 wt % of ACN with regard to the total amount of solvent.

The molar ratio of compounds of formula I to $Br_2$ may be from 5:1 to 1:5, preferably from 1:1 to 1:5, more preferably from 1:1 to 1:2, and most preferably from 1:1 to 1:1.5, especially preferably from 1:1 to 1:1.4, and in particular from 1:1 to 1:1.3.

The concentration of compounds of formula I at the beginning of the reaction with regard to the total amount of solvent may be from 1 to 90 wt %, preferably 10 to 80 wt %, more preferably from 10 to 50 wt %, and in particular 15 to 20 wt %.

The molar ratio of DIPEA to compounds of formula I is usually from 10:1 to 1:2, preferably from 5:1 to 1:1, more preferably from 3:1 to 1:1, most preferably from 2:1 to 1:1. The molar ratio of DI PEA to compounds of formula II may be at least 1:1, more preferably at least 1.5:1.

Steps A and B may be carried out as a one-pot process. The term "one-pot process" refers to a process, wherein the products of a first reaction step, e.g. compounds of formula I in Step A, are directly used in a second reaction step, e.g. in Step B, without intermediate purification steps. Accordingly, the products of the first process may remain in their mother liquor and are applied as such in the second process. The first and second reaction step may be carried out in the same reactor, or in different reactors. Preferably they are carried out in one reactor.

In case Steps A and B are carried out as one-pot process, the solvent for both processes is the same and remains approximately unchanged in its composition, and the whole amount of DIPEA—otherwise distributed between Step A and Step B—is added directly at the beginning of Step A. Accordingly, the molar ratio of DIPEA to compounds of formula II in Step A may be from 10:1 to 2:1, more preferably from 6:1 to 3:1, most preferably from 5:1 to 3:1. Usually the molar ratio of DIPEA to compounds of formula II in Step A in case Step A and Step B are carried out as a one-pot process is at least 2:1, preferably at least 3:1, most preferably at least 4:1.

Suitable catalysts may be added in Step B at a sub-stoichiometric ratio with regard to compounds of formula I. The molar ratio of the catalyst to compounds of formula I may be from $1:10^6$ to 1:10, preferably from $1:10^5$ to 1:100, more preferably from 1:1000 to 1:100. In one embodiment, the catalyst is DMF.

The reaction mixtures after Step A and Step B may be worked up in a customary manner, for example by mixing with water, separating the phases and, if appropriate, chromatographic purification of the crude products. Usually, all aprotic polar solvent, in particular all ACN, is removed from the reaction mixture after Step B by distillation and replaced by a solvent suitable for Step C. Subsequently, water may be added and the biphasic composition heated to 50° C. to 80° C., preferably 60° C. to 70° C. The aqueous layer is then removed, and the organic layer containing compounds of formula III is dried, e.g. by addition of a hygroscopic material. Compounds of formula III may be obtained by crystallization from the organic layer, or by removal of the organic solvent.

Compounds of formula IV are produced in Process C comprising the reaction of compounds of formula III with di($C_1$-$C_4$-alkoxy)methane and $POCl_3$, or $POCl_3$ and DMF (Vilsmeier reagent) in the presence of DIPEA

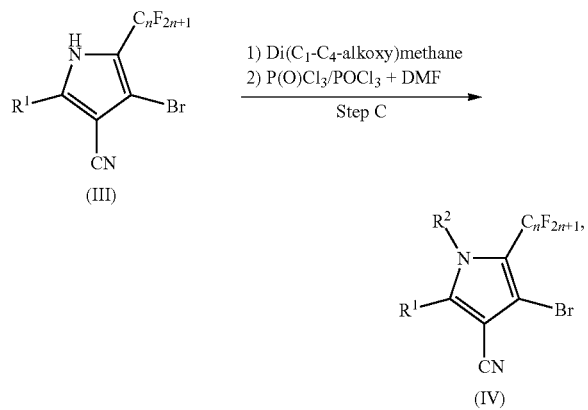

wherein $R^2$ is $C_1$-$C_4$-alkoxymethyl; and wherein the other variables have a meaning as defined for compounds of formula I. Typically, Step C is carried out in the presence of DIPEA as the only base and no other additional bases are present, in particular not triethylamine. Preferably, the ratio of DIPEA to other bases in Step C is at least than 5:1, preferably at least 10:1, and in particular at least 100:1.

Step C is usually carried out at temperatures of from 30° C. to 80° C., preferably from 40° C. to 70° C., in an inert solvent. The di($C_1$-$C_4$-alkoxy)methane is typically diethoxymethane, in which case $R^2$ is $CH_3CH_2OCH_2$. Di($C_1$-$C_4$-alkoxy)methane compounds are commercially available, or can be prepared as described in Pathak D., Gerald J., Synthetic Communications, 2003, vol. 33(9), pp. 1557-1561.

Suitable inert solvents are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; nitriles, preferably $C_1$-$C_6$-nitriles, such as ACN, and $CH_3CH_2CN$; amides and urea derivatives, preferably DMF, NMP, DMA, DMI, DMPU, HMPA; moreover DMSO, and sulfolane. Mixtures of the above solvents are also possible.

In one embodiment, the inert solvent comprises aliphatic $C_5$-$C_{16}$-hydrocarbons, aromatic $C_6$-$C_{10}$-hydrocarbons, halogenated aliphatic $C_1$-$C_6$-alkanes, halogenated aromatic $C_6$-$C_{10}$-hydrocarbons, $C_1$-$C_6$-nitriles, amides, or a mixture thereof. In another embodiment, the inert solvent comprises aliphatic $C_5$-$C_{16}$-hydrocarbons, aromatic $C_6$-$C_{10}$-hydrocarbons, $C_1$-$C_6$-nitriles, DMF, or a mixture thereof. In another embodiment, the inert solvent comprises aromatic $C_6$-$C_{10}$-hydrocarbons, ACN, DMF, or a mixture thereof. In another embodiment, the inert solvent comprises benzene, toluene, xylene, ACN, DMF, or a mixture thereof. In another embodiment, the inert solvent comprises toluene, ACN, DMF, or a mixture thereof. In another embodiment, the inert solvent comprises toluene.

The molar ratio of compounds of formula III to di($C_1$-$C_4$-alkoxy)methane may be from 5:1 to 1:5, preferably from 1:1 to 1:5, and most preferably from 1:1 to 1:2. The molar ratio is usually up to 1:1, more preferably up to 1:1.5.

The molar ratio of DIPEA to compounds of formula III is usually from 10:1 to 1:2, preferably from 5:1 to 1:1, more preferably from 3:1 to 1:1, most preferably from 2:1 to 1:1. The molar ratio of DIPEA to compounds of formula III may be at least 1:1, more preferably at least 1.5:1.

In one embodiment, compounds of formula III are reacted with $POCl_3$. In this case, the molar ratio of $POCl_3$ to compounds of formula III may be from 1:2 to 10:1, preferably from 1:1 to 5:1, more preferably from 1:1 to 3:1, and in particular from 1:1 to 2:1. In another embodiment, compounds of formula III are reacted with Vilsmeier reagent, i.e. a mixture of DMF and $POCl_3$. The molar ratio of DMF to $POCl_3$ may be from 0.1:5 to 5:1, preferably from 0.1:3 to 3:1, and most preferably 0.1:2 to 1:1. The molar ratio of $POCl_3$ in the Vilsmeier reagent to compounds of formula III may be from 1:2 to 10:1, preferably from 1:1 to 5:1, more preferably from 1:1 to 3:1, and in particular from 1:1 to 2:1.

Compounds of formula II may be produced in a Step D by reaction of compounds of formula V

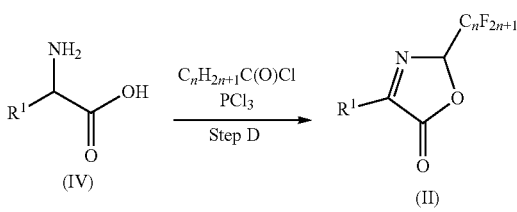

with $C_nF_{2n+1}C(O)Cl$ and $PCl_3$; wherein the variables have a meaning as defined for compounds of formula I. Compounds of formula V can be derived from commercially available phenylglycine. Para-chlorophenylglycine is equally commercially available. $C_nF_{2n+1}C(O)Cl$ usually refers to $CF_3C(O)Cl$, in which case the variable n in formulae II and V is 1.

Step D is usually carried out at temperatures of from 20° C. to 80° C., preferably from 30° C. to 70° C., in an inert solvent, and optionally in the presence of a catalyst. Typically, no base is added in Step D.

Suitable inert solvents are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, preferably $C_1$-$C_6$-cycloalkyl ethers, $C_1$-$C_6$-alkyl-$C_1$-$C_6$-alkyl ethers, $C_1$-$C_6$-alkyl-$C_3$-$C_6$-cycloalkyl ethers, $C_1$-$C_6$-polyol-$C_1$-$C_6$-alky ethers, and $C_1$-$C_6$-alkyl-$C_6$-$C_{10}$-aryl ethers, such as $CH_3CH_2OCH_2CH_3$, $(CH_3)_2CHOCH(CH_3)_2$, $CH_3OC(CH_3)_3$ (MTBE), $CH_3OCH_3$ (DME), $CH_3OCH_2CH_2OCH_3$, $CH_3OC(CH_3)_2CH_2CH_3$, dioxane, anisole, 2-methyltetrahydrofuran, tetrahydrofuran (THF), and diethylene glycol; esters, preferably esters of aliphatic $C_1$-$C_6$-alcohols with aliphatic $C_1$-$C_6$-carboxylic acids, esters of aromatic $C_6$-$C_{10}$-alcohols with aromatic $C_6$-$C_{10}$-carboxylic acids, cyclic esters of ω-hydroxy-$C_1$-$C_6$-carboxylic acids, such as $CH_3C(O)OCH_2CH_3$, $CH_3C(O)OCH_3$, $CH_3C(O)OCH_2CH_2CH_3$, $CH_3C(O)OCH(CH_3)CH_2CH_3$, $CH_3C(O)OC(CH_3)_3$, $CH_3CH_2CH_2C(O)OCH_2CH_3$, $CH_3CH(OH)C(O)OCH_2CH_3$, $CH_3CH(OH)C(O)OCH_3$, $CH_3C(O)OCH_2CH(CH_3)_2$, $CH_3C(O)OCH(CH_3)_2$, $CH_3CH_2C(O)OCH_3$, benzyl benzoate, and γ-butyrolactone; carbonates, such as ethylene carbonate, propylene carbonate, $CH_3CH_2OC(O)OCH_2CH_3$, and $CH_3OC(O)OCH_3$; nitriles, preferably $C_1$-$C_6$-nitriles, such as ACN, and $CH_3CH_2CN$; ketones, preferably $C_1$-$C_6$-alkyl-$C_1$-$C_6$-alkyl ketones, such as $CH_3C(O)CH_3$, $CH_3C(O)CH_2CH_3$, $CH_3CH_2C(O)CH_2CH_3$, and $CH_3C(O)C(CH_3)_3$ (MTBK); amides and urea derivatives, preferably DMF, NMP, DMA, DMI, DMPU, HMPA; moreover DMSO, and sulfolane. Mixtures of the above solvents are also possible.

In one embodiment, the inert solvent comprises aliphatic hydrocarbons, aromatic hydrocarbons, nitriles, or mixtures thereof. In another embodiment, the inert solvent comprises aliphatic $C_5$-$C_{16}$-hydrocarbons, aromatic $C_6$-$C_{10}$-hydrocarbons, $C_1$-$C_6$-nitriles, or a mixture thereof. In another embodiment, the inert solvent comprises aromatic $C_6$-$C_{10}$-hydrocarbons, $C_1$-$C_6$-nitriles, or a mixture thereof. In another embodiment, the inert solvent comprises benzene, toluene, xylene, ACN, or a mixture thereof. In another embodiment, the inert solvent comprises a mixture of toluene and ACN. In another embodiment, the inert solvent comprises ACN.

Suitable inert solvents usually comprise a polar aprotic solvent. In one embodiment, the inert solvent is a mixture of a polar aprotic solvent and a non-polar solvent. In another embodiment, the inert solvent only consists of non-polar solvents. Examples of polar aprotic solvents are esters, ketones, nitriles, amides and urea derivatives, DMSO, and sulfolane. Examples of non-polar solvents are aliphatic hydrocarbons, aromatic hydrocarbons, and ethers.

In case the solvent comprises a one polar aprotic solvent, the concentration of the sum of all polar aprotic solvents with regard to the total amount of solvent is at least 20 wt %, preferably at least 30 wt %, more preferably at least 40 wt %, most preferably at least 60 wt %, and in particular at least 70 wt %. The sum of all polar aprotic solvents with regard to the total amount of solvent may be from 10 to 99 wt %, preferably from 20 to 95 wt %, more preferably from 25 to 90 wt %, most preferably from 50 to 80 wt %. In one embodiment, the solvent comprises at least 40 wt %, preferably at least 50 wt % of ACN with regard to the total amount of solvent.

Suitable catalysts may be added in Step D at a substoichiometric ratio with regard to compounds of formula V. The molar ratio of the catalyst to compounds of formula V may be from $1:10^6$ to 1:10, preferably from $1:10^5$ to 1:100, more preferably from 1:1000 to 1:100. In one embodiment, the catalyst is DMF.

The molar ratio of compounds of formula V to $C_nF_{2n+1}C(O)Cl$ may be from 1:2 to 5:1, preferably from 1:1 to 3:1, more preferably from 1:1 to 2:1. The molar ratio of $PCl_3$ to compounds of formula V may be from 1:10 to 1:1, preferably from 1:5 to 1:1, more preferably from 1:3 to 1:2.

The concentration of compounds of formula V may be from 10 to 80 wt % with regard to the total weight of solvent, preferably from 10 to 50 wt %, more preferably from 20 to 40 wt %. Typically, $PCl_3$ is added to compounds of formula V before the addition of $C_nF_{2n+1}C(O)Cl$ over a time of from 5 min to 60 min. $C_nF_{2n+1}C(O)Cl$ is usually added over a time of from 30 min to 120 min. Depending on the physical state of $C_nF_{2n+1}C(O)Cl$ at 25° C., the compound may be added as a gas subsurface to the reaction mixture, or may be added as a liquid.

Steps A and D may be carried out as a one-pot process, i.e. compounds of formula II in Step D, are directly used in Step A, without intermediate purification steps. Accordingly, the compounds of formula II produced in Step D may remain in their mother liquor and are applied as such in Step A. Steps A and D may be carried out in the same reactor, or in different reactors. Preferably they are carried out in one reactor. In case Steps A and D are carried out as one-pot process, the whole amount of DIPEA is added during Step A.

The following definitions of the variables are the meanings and preferred meanings for all formulae in which they appear.

$R^1$ is usually phenyl, substituted with none, one, or more, same, or different $R^{11}$. Preferably, $R^1$ is phenyl, which is substituted with one $R^{11}$, more preferably substituted with one $R^{11}$ in para position, i.e. a 4-$R^{11}$-phenyl substituent.

$R^{11}$ is usually F, Cl, Br, I, CN, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkyl-C(O)O, $C_1$-$C_4$-haloalkyl-C(O)O; or two substituents $R^{11}$ situated at adjacent phenyl ring-atoms together are a group —$OCH_2O$—, —$OCF_2O$, or —$CH=CH$—

CH=CH—, and form, together with the carbon atoms to which they are attached a 5- or 6-membered ring.

In one embodiment, $R^{11}$ is F, Cl, Br, I, CN, $NO_2$, OH, $C_1$-$C_4$-alkyl, $C_1$-$C_4$-haloalkyl, $C_1$-$C_4$-alkoxy, or $C_1$-$C_4$-haloalkoxy. In another embodiment, $R^{11}$ situated at adjacent phenyl ring-atoms together are a group —$OCH_2O$—, —$OCF_2O$—, or —CH=CH—CH=CH—, and form, together with the carbon atoms to which they are attached a 5- or 6-membered ring. In another embodiment $R^{11}$ is F, $C_1$, Br, I, CN, $NO_2$, or OH. In another embodiment $R^{11}$ is F, Cl, Br, or I. In another embodiment $R^{11}$ is Cl The variable n is 1, 2, or 3, preferably 1.

$R^2$ is $C_1$-$C_4$-alkoxymethyl, preferably $CH_3CH_2OCH_2$.

Preferably, compounds of formula I relate to the compound of formula Ia, falling under the definition of compounds of formula I

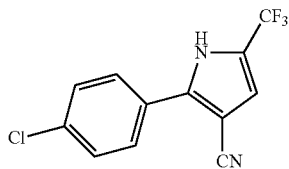

(Ia)

Preferably, compounds of formula II relate to the compound of formula IIa falling under the definition of compounds of formula II

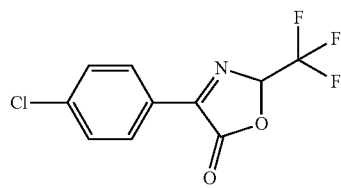

IIa

Preferably, compounds of formula III relate to Tralopyril, corresponding to compound IIIa and falling under the definition of compounds of formula III

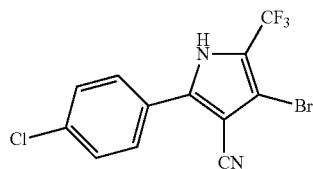

(IIIa)

Preferably, compounds of formula IV relate to Chlorfenapyr, corresponding to compound IVa and falling under the definition of compounds of formula IV

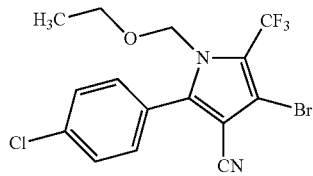

(IVa)

Preferably, compounds of formula V relate to the compound of formula Va, falling under the definition of compounds of formula V

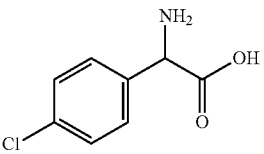

(Va)

The organic moieties mentioned herein for the definitions of the variables are—like the term halogen—collective terms for individual listings of the individual group members. The prefix $C_n$-$C_m$ indicates in each case the possible number of carbon atoms in the group. The term "halogen" denotes in each case F, Br, Cl, or I, especially F, Cl, or Br, and in particular Cl. The term "alkyl" as used herein denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are $CH_3$, $CH_3CH_2$, $CH_3CH_2CH_2$, $(CH_3)_2CH$, $CH_3CH_2CH_2CH_2$, $CH_3CH_2CH(CH_3)$, $(CH_3)_2CHCH_2$, $(CH_3)_3C$, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl. The term "haloalkyl" as used herein and in the haloalkyl moieties of haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as $CH_2F$, $CHF_2$, $CF_3$, $CHFCH_3$, $CH_2CH_2F$, $CH_2CHF_2$, $CH_2CF_3$, $CF_2CF_3$, and the like. The term "alkoxy" as used herein denotes in each case a straight-chain or branched alkyl group which is bonded via an oxygen atom and has usually from 1 to 10 carbon atoms, frequently from 1 to 6 carbon atoms, preferably 1 to 4 carbon atoms. Examples of an alkoxy group are $CH_3O$, $CH_3CH_2O$, $CH_3CH_2CH_2O$, $(CH_3)_2CHO$, $CH_3CH_2CH_2CH_2O$, $CH_3CH_2C(CH_3)O$, $(CH_3)_2CHCH_2O$, $(CH_3)_3C$, and the like. The term "alkoxyalkyl" as used herein refers to alkyl usually comprising 1 to 10, frequently 1 to 4, preferably 1 to 2 carbon atoms, wherein 1 carbon atom carries an alkoxy radical usually comprising 1 to 4, preferably 1 or 2 carbon atoms as defined above. Examples are $CH_3OCH_2$, $C_2H_5OCH_2$, $CH_3OCH_2CH_2$, and $CH_3CH_2OCH_2CH_2$. The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular F-atoms. Preferred haloalkoxy moieties include $C_1$-$C_4$-haloalkoxy, in particular $C_1$-$C_2$-fluoroalkoxy, such as $CH_2FO$, $CHF_2O$, $CF_3O$, $CH_3CHFO$, $CH_2FCH_2O$, $CHF_2CH_2O$, $CF_3CH_2O$, $CHClFCH_2O$, $CClF_2CH_2O$, CCl$_2$FCH$_2$O, CCl$_3$CH$_2$O, CF$_3$CF$_2$O and the like. The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl (CCSH$_4$), cyclobutyl, cyclopentyl, cyclohexyl, cycloheptyl, cyclooctyl, cyclononyl and cyclodecyl or cyclopropyl, cyclobutyl, cyclopentyl and cyclohexyl. The term "substituted" refers in each case to a substitution by one, or more, same or different substituents. The term "halogenated" refers to a partial, of complete substitution with halogen.

The term "the solvent comprises" usually relates to a concentration of at least 50 wt % of the respective compound with regard to the total amount of solvent, preferably at least 80 wt %, in particular 100 wt %. compounds of formula I, II, III, and IV may be present in the form of their salts, tautomers, and stereoisomers. Such salts will typically be obtained by reacting the compounds with an acid, if the compound has a basic functionality such as an amine, or by reacting the compounds with a base, if the compound has an acidic functionality. Cations, which stem from a base, with which the compounds of the present invention are reacted, are e.g. alkali metal cations M$_a^+$, alkaline earth metal cations M$_{ea}^{2+}$ or ammonium cations NR$_4^+$, wherein the alkali metals are preferably sodium, potassium or lithium and the alkaline earth metal cations are preferably magnesium or calcium, and wherein the substituents R of the ammonium cation NR$_4^+$ are preferably independently selected from H, C$_1$-C$_{10}$-alkyl, phenyl and phenyl-C$_1$-C$_2$-alkyl. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium (NH$_4^+$) and substituted ammonium in which one to four of the hydrogen atoms are replaced by C$_1$-C$_4$-alkyl, C$_1$-C$_4$-hydroxyalkyl, C$_1$-C$_4$-alkoxy, C$_1$-C$_4$-alkoxy-C$_1$-C$_4$-alkyl, hydroxy-C$_1$-C$_4$-alkoxy-C$_1$-C$_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzl-triethylammonium, furthermore phosphonium ions, sulfonium ions, preferably tri(C$_1$-C$_4$-alkyl)sulfonium, and sulfoxonium ions, preferably tri(C$_1$-C$_4$-alkyl)sulfoxonium. Anions, which stem from an acid, with which the compounds of the present invention have been reacted, are e.g. chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of C$_1$-C$_4$-alkanoic acids, preferably formate, acetate, propionate and butyrate. Tautomers of the compounds of the present invention include keto-enol tautomers, imine-enamine tautomers, amide-imidic acid tautomers and the like. The compounds of the present invention cover every possible tautomer. The term "stereoisomers" encompasses both optical isomers, such as enantiomers or diastereomers, the latter existing due to more than one centre of chirality in the molecule, as well as geometrical isomers (cis/trans isomers). Depending on the substitution pattern, the compounds of the present invention may have one or more centres of chirality, in which case they may be present as mixtures of enantiomers or diastereomers. The terms compounds of formula I, compounds of formula II, compounds of formula III, and compounds of formula IV comprise both the pure enantiomers or diastereomers of the respective compounds, and their mixtures. The term "polar aprotic solvents" generally refers to solvents that are characterized by a dipole moment of at least 4×10$^{-30}$ Cm, preferably at least 5×10$^{-30}$ Cm, more preferably at least 5.5×10$^{-30}$ Cm. Accordingly, the term "non-polar solvents" generally refers to solvents that are characterized by a dipole moment of below 4×10$^{-30}$ Cm (Coulomb-meter), preferably up to 3×10$^{-30}$ Cm, more preferably up to 1×10$^{-30}$ Cm, and in particular below 0.5×10$^{-30}$ Cm. The term "POCl$_3$" refers to phosphoryl chloride. The term "reaction step" generically refers to Step A, Step B, Step C, or Step D, as defined above. The terms "p-chlorophenyl" or "para-chlorophenyl" refer to 4-chlorophenyl. The term "Vilsmeier" relates to a mixture of DMF and POCl$_3$, wherein the molar ratio of DMF to POCl$_3$ may be from 1:10 to 10:1, preferably from 1:3 to 3:1, and in particular 1:1. The term "DIPEA" refers to diisopropylethylamine, which term is synonym with the terms "EDIPA", "((CH$_3$)$_2$CH)$_2$CH$_3$CH$_2$N", and "Hünig's base". Accordingly, DIPEA relates to compounds of formula VI

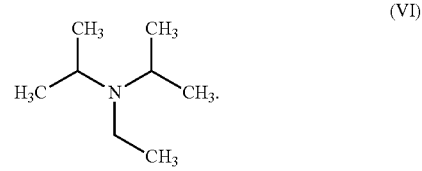

(VI)

DIPEA is a commercially available base. The term "base", as used in this application, does not relate to compounds of formulae I, II, III, IV, or V. The term "compounds of formula X", wherein X is a variable assigned to a specific formula, comprises a stereoisomer, salt, tautomer or N-oxide thereof. It is of course to be understood that tautomers can only be present, if the structure allows for tautomers such as keto-enol tautomers, imine-enamine tautomers, amide-imidic acid tautomers or the like. Otherwise, the term "compounds of formula X" does not encompass tautomers. Furthermore, it is to be understood that stereoisomers are only possible, if there is at least one centre of chirality in the molecule or if geometrical isomers (cis/trans isomers) can be formed. The compounds may be amorphous or may exist in one or more different crystalline states (polymorphs) which may have different macroscopic properties such as stability or show different biological properties such as activities. The present invention relates to methods featuring amorphous and crystalline compounds, mixtures of different crystalline states of the respective compound, as well as amorphous or crystalline salts thereof. Salts of the compounds are preferably agriculturally acceptable salts. They can be formed in a customary manner, e.g. by reacting the compound with an acid of the anion in question if the compound has a basic functionality. Agriculturally useful salts of the compounds encompass especially the acid addition salts of those acids whose cations and anions, respectively, have no adverse effect on the mode of action of the compounds. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of C$_1$-C$_4$-alkanoic acids, preferably formate, acetate, propionate and butyrate. They can be formed by reacting the compounds with an acid of the corresponding anion, preferably of hydrochloric acid, hydrobromic acid, sulfuric acid, phosphoric acid or nitric acid. The term "N-oxide" includes any compounds which have at least one tertiary nitrogen atom that is oxidized to an N-oxide moiety. Of course, N-oxides can only be formed, if a nitrogen atom is present within the compounds.

Process A comprises Step A. In one embodiment, Process A comprises Step D, followed by Step A. Process B comprises Step B. In one embodiment, Process B comprises Step A, followed by Step B. In another embodiment, Process B comprises Step D, followed by Step A, which is turn followed by Step B. Process C comprises Step C. In one embodiment, Process C comprises Step B, followed by Step C. In another embodiment, Process C comprises Step A, followed by Step B, which is in turn followed by Step C. In yet another embodiment, Process C comprises Step D, followed by Step A, followed by Step B, which is in turn followed by Step C.

The invention also relates to the use of DIPEA as a base in the production of compounds of formula I, in particular in Step A. It also relates to the use of DIPEA as a base in the production of compounds of formula III, in particular in Step B. It also relates to the use of DIPEA as a base in the production of compounds of formula IV, in particular in Step C.

In general, the reaction steps performed in the processes A, B, and C are performed in reaction vessels customary for such reactions, the reactions being carried out in a continuous, semi-continuous or batchwise manner. In general, the particular reactions will be carried out under atmospheric pressure. The reactions may, however, also be carried out under reduced pressure. The temperatures and the duration times of the reactions may be varied in broad ranges, which the person skilled in the art knows from analogous reactions. The temperatures often depend on the reflux temperature of the solvents. Other reactions are preferably performed at room temperature, i.e. at about 25° C., or under ice cooling, i.e. at about 0° C. The end of the reaction can be monitored by methods known to a person skilled in the art, e.g. thin layer chromatography or HPLC. If not otherwise indicated, the reactants can in principle be contacted with one another in any desired sequence. The person skilled in the art knows when the reactants or reagents are moisture sensitive, so that the reaction should be carried out under protective gases such as under a nitrogen atmosphere, and dried solvents should be used. The person skilled in the art also knows the best work-up of the reaction mixture after the end of the reaction.

The following examples illustrate the invention.

EXAMPLES

Characterization

The characterization can be done by coupled High-Performance-Liquid-Chromatography at a UV-VIS detector at a wavelength of 220 nm, utilizing known and analytically verified standards for all compounds and intermediates. The gradient utilized 45 vol % ACN/55 vol % pH 2.1 aqueous phosphate buffer solution as mobile phase A and 100% ACN for mobile phase B. The column used contained a reversed phase C-18 material.

Abbreviations used are: h for hour(s), min for minute(s), eq for equivalent(s), hPa for hectopascal. $NaOH_{aq}$ is a solution of NaOH in water. TFA-Cl is trifluoroacetyl chloride. PCPG is 4-parachlorophenylglycine.

Example-1: Preparation of Tralopyril and Chlorfenapyr by Using DIPEA as a Base

Step A1: Preparation of 4-(4-chlorophenyl)-2-(trifluoromethyl)-2H-oxazol-5-one

To a pre-weighed reactor equipped with mechanical stirrer, condenser, thermocouple, and addition funnel was added PCPG (41.3 g, 97.7% pure) under argon gas atmosphere. A solution consisting of ACN (86.8 g) and toluene (37.2 g), as well as DMF (0.13 g) was added to the reactor. The resulting mixture was stirred as a slurry. $PCl_3$ (13.55 g) was charged over 30 min via a funnel to the slurry, while maintaining the reaction temperature at 30° C. to 35° C. Immediately after $PCl_3$ addition was complete, TFA-Cl gas (31.6 g) was added subsurface to the reactor over the course of 1 h, whereby the temperature was kept at 40° C. to 60° C. After completion of the addition of TFA-Cl, the resulting yellow slurry was held at 45° C. for an additional 8 h. Analysis of the slurry by HPLC resulted in 99.9% yield of 4-(4-chlorophenyl)-2-(trifluoromethyl)-2H-oxazol-5-one. The reaction temperature was then raised to from 68° C. to 82° C. and held for 90 min. The slurry was then allowed to cool to 25° C.

Step A2: Preparation of 2-(4-chlorophenyl)-5-(trifluoromethyl)-1H-pyrrole-3-carbonitrile To the reactor containing the slurry of 4-(4-chlorophenyl)-2-(trifluoromethyl)-2H-oxazol-5-one of Step A1 was added a solution of 2,3-dichloropropionitrile (28.51 g) in DMF (21.34 g). Subsequently, DIPEA (102.8 g) was added to the reactor over 38 min while keeping a reaction temperature of 20° C. to 55° C. The reactor then contained a dark solution with some white vapor above the solution, which was drawn into the condenser. The solution was kept at 35° C. for 60 min. Analysis of the solution by HPLC resulted in a yield of 2-(4-chlorophenyl)-5-(trifluoromethyl)-1H-pyrrole-3-carbonitrile of 89.8% with regard to the amount of PCPG in Step A1.

Step A3: Preparation of Tralopyril

To the reactor containing the solution of 2-(4-chlorophenyl)-5-(trifluoromethyl)-1H-pyrrole-3-carbonitrile of Step A2 was added $Br_2$ (39.9 g) over 20 min while keeping the reaction temperature at 30° C. to 40° C. White fog was produced by the reaction mixture, which had turned into a dark solution. After complete addition of $Br_2$, the reaction temperature was held at 35° C. for 40 min. Toluene (144 g) was added to the solution, followed by distillation at 80° C. and a pressure of 393 hPa to 407 hPa to remove the ACN from the reaction mixture. An amount of toluene equal to the amount removed by distillation, as well as deionized $H_2O$ (100 g) was then added to the reaction mixture, which was stirred at 80° C. for 15 min and split into an Aqueous Layer I and an organic layer in a pre-heated separatory funnel. Analysis of the organic layer by HPLC resulted in a yield of Tralopyril of 88.2% with regard to the amount of PCPG in Step A1. Residual water in the organic phase was distilled off at reduced pressure at 65° C., upon which the removed solvent volume was balanced by the addition of an equivalent volume of toluene. The solution of Tralopyril in toluene was then cooled to 25° C.

Step A4: Preparation of Chlorfenapyr

The solution of Tralopyril in toluene of Step A3 was added into a reactor, followed by addition of $(CH_3CH_2O)_2$ CH$_2$ (28.9 g). P(O)Cl$_3$ (31.9 g) was then added to the reactor over 24 min while maintaining a reaction temperature at 45° C. to 55° C. After addition had been completed, the reaction temperature was maintained at 45° C. to 65° C. for 60 min. DIPEA (40.8 g) was subsequently charged over 10 min while maintaining a reaction temperature of 40° C. to 50° C. The reaction mixture was subsequently kept at 45° C. for 1 h. By then, the reaction mixture had turned into a dark solution. Demineralized H$_2$O (38.9 g) and NaOH$_{aq}$ (50 wt %, 17.4 g) were added and the resulting biphasic mixture was heated to 75° C. After maintaining that temperature for 10 min, the mixture was split into an Aqueous Layer II and an organic layer in a pre-heated separation funnel. Analysis of the organic phase by HPLC resulted in a yield of Chlorfenapyr of 87.8% with regard to the amount of PCPG in Step A1.

Step A5: Recovery of DIPEA

To the Aqueous Layer I from Step A3 was added NaOH$_{aq}$ (50 wt %, 85.1 g) and H$_2$O (39.1 g). The resulting composition was stirred at 70° C., upon which the bottom layer was discarded. The top layer afforded 88 g of DIPEA with a purity of 92% determined by GC, containing approximately 8 wt % of toluene and below 0.2 wt % of H$_2$O. To the Aqueous Layer II from Step A4 was added NaOH$_{aq}$ (50 wt %, 60.6 g) and H$_2$O (19.5 g). The resulting composition was stirred at 70° C. for 30 min, upon which the bottom layer was discarded. The top layer afforded 57 g of DIPEA with a purity of 95% determined by GC, containing approximately 5 wt % of toluene and below 0.2 wt % of H$_2$O. The overall recovery rate of DIPEA was 95%. Due to the low water content of the thus recovered DIPEA, no distillation was required.

Comparative Example-2: Preparation of Tralopyril and Chlorfenapyr by Using TEA as a Base Step B1: Preparation of 4-(4-chlorophenyl)-2-(trifluoromethyl)-2H-oxazol-5-one To a pre-weighed reactor equipped with mechanical stirrer, condenser, thermocouple, and addition funnel was added PCPG (38.0 g, 98.6% pure) under argon gas atmosphere. A solution consisting of ACN (80.5 g) and toluene (34.5 g), as well as DMF (0.13 g) was added to the reactor. The resulting mixture was stirred as a slurry. PCl$_3$ (12.6 g) was charged over 30 min via a funnel to the slurry, while maintaining the reaction temperature at 30° C. to 35° C. Immediately after PCl$_3$ addition was complete, TFA-Cl gas (28.4 g) was added subsurface to the reactor over the course of 1 h, whereby the reaction temperature was kept at 40° C. to 60° C. After completion of the addition of TFA-Cl, the resulting yellow slurry was held at 45° C. for an additional 8 h. Analysis of the slurry by HPLC resulted in 99.9% yield of 4-(4-chlorophenyl)-2-(trifluoromethyl)-2H-oxazol-5-one. The reaction temperature was then raised to from 68° C. to 82° C. and held for 90 min. The slurry was then allowed to cool to 25° C.

Step B2: Preparation of 2-(4-chlorophenyl)-5-(trifluoromethyl)-1H-pyrrole-3-carbonitrile To the reactor containing the slurry of 4-(4-chlorophenyl)-2-(trifluoromethyl)-2H-oxazol-5-one of Step B1 was added a solution of 2,3-dichloropropionitrile (22.51 g) in DMF (22.96 g). Subsequently, TEA (75.0 g) was added to the reactor over 38 min while keeping a reaction temperature of 20° C. to 55° C. The reactor then contained a yellow slurry and white vapor above the slurry, which was drawn into the condenser. The slurry was kept at 35° C. for 60 min. Analysis of the slurry by HPLC resulted in a yield of 2-(4-chlorophenyl)-5-(trifluoromethyl)-1H-pyrrole-3-carbonitrile of 79.7% with regard to the amount of PCPG in Step B1.

Step B3: Preparation of Tralopyril

To the reactor containing the slurry of 2-(4-chlorophenyl)-5-(trifluoromethyl)-1H-pyrrole-3-carbonitrile of Step B2 was added Br$_2$ (37.1 g) over 20 min while keeping the reaction temperature at 30° C. to 40° C. White fog was produced by the reaction mixture, which had turned into a dark thick slurry. After complete addition of Br$_2$, the reaction temperature was held at 35° C. for 40 min. Toluene (144 g) was added to the slurry, followed by distillation at 80° C. and a pressure of 393 hPa to 407 hPa to remove the ACN from the reaction mixture. The amount of toluene removed by distillation, as well as deionized H$_2$O (109 g) was then added to the reaction mixture, which was stirred at 80° C. for 15 min and split into an Aqueous Layer III and an organic layer in a pre-heated separatory funnel. Analysis of the organic layer by HPLC resulted in a yield of Tralopyril of 75.3% with regard to the amount of PCPG in Step B1. Residual water in the organic phase was distilled off at reduced pressure at 65° C., upon which the removed solvent volume was balanced by the addition of an equivalent volume of toluene. The solution of Tralopyril in toluene was then cooled to 25° C.

Step B4: Preparation of Chlorfenapyr

The solution of Tralopyril in toluene of Step B3 was added into a reactor, followed by addition of (CH$_3$CH$_2$O)$_2$CH$_2$ (26.9 g). P(O)Cl$_3$ (29.7 g) was then added to the reactor over 24 min while maintaining a reaction temperature of 45° C. to 55° C. The reaction temperature was then maintained at 45° C. to 65° C. for 60 min. TEA (29.8 g) was subsequently charged over 10 min while maintaining a reaction temperature of 40° C. to 50° C. The reaction mixture was then kept at 45° C. for 1 h. By then, the reaction mixture had turned into a dark slurry. Demineralized H$_2$O (80 g) and NaOH$_{aq}$ (50 wt %, 16.2 g) were then added and the resulting biphasic mixture was heated to 75° C. After maintaining that temperature for 10 min, the mixture was split into an Aqueous Layer IV and an organic layer in a preheated separation funnel. Analysis of the organic phase by HPLC resulted in a yield of Chlorfenapyr of 75.1% with regard to the amount of PCPG in Step B1.

Step B5: Recovery of TEA

To the Aqueous Layer III from Step B3 was added NaOH$_{aq}$ (50 wt %, 79.2 g) and H$_2$O (36.4 g). The resulting composition was stirred at 70° C., upon which the bottom layer was discarded. The top layer afforded 68 g of TEA with a purity of 94% determined by GC, containing approximately 3.5 wt % of toluene and 2.2 wt % of H$_2$O. To the Aqueous Layer IV from Step B4 was added NaOH$_{aq}$ (50 wt %, 65.4 g) and H$_2$O (18.2 g). The resulting composition was stirred at 70° C. for 30 min, upon which the bottom layer was removed. The top layer afforded 25.6 g of TEA with a purity of 94% determined by GC, containing approximately 2.4 wt % of toluene and 3.0 wt % of H$_2$O. Because of the high water content of the thus recovered TEA, the combined crude TEA is distilled at atmospheric pressure at a temperature of from 72° C. to 92° C. The first 15 g of distillate was discarded due to high water content. The remaining distillate contained 74.4 g of TEA with a purity of 95% determined by GC, containing below 0.2 wt %. The overall recovery rate of TEA was 67.4%.

Example-3: Comparison of Bases in Step A

Pyridine, 1,2-diazabicyclo[2,2,2]octane, and tripropylamine were used as bases in Step A. The experiments were conducted in analogy to Step A2 in Example 1. Accordingly, the ratio of the bases to 4-(4-chlorophenyl)-2-(trifluoromethyl)-2H-oxazol-5-one was approximately 3.65. The following yields of 2-(4-chlorophenyl)-5-(trifluoromethyl)-1H-pyrrole-3-carbonitrile could be obtained and calculated with regard to the amount of PCPG added in Step A1:

TABLE 1

Yields of 2-(4-chlorophenyl)-5-(trifluoromethyl)-1H-pyrrole-3-carbonitrile depending on the base.

| Base | Yield |
| --- | --- |
| Pyridine | 68.1% |
| 1,4-diazabicyclo[2,2,2]octane | 67.1% |
| Tripropylamine | 57.8% |

Example-4: Visual Assessment of Step A

The reaction mixtures of Steps A2 in Example 1 and B2 in Comparative Example 2 were visually assessed. In case of A2, a clear and easy-to-handle solution and little fog production was observed. In case of B2, a thick slurry and lots of fog was visible, which completely filled up the condenser. FIGS. 1 and 2 showed pictures that were taken from the respective reaction vessels.

Example-5: Visual Assessment of Step B

The reaction mixtures of Steps A3 in Example 1 and B3 in Comparative Example 2 were visually assessed. In case of A3, little fog production was observed. In case of B3, lots of fog was visible, which completely filled up the condenser. FIG. 3 showed a picture that were taken from the respective reaction vessels during the reaction.

Example-6: Visual Assessment of Step C

The reaction mixtures of Steps A4 in Example 1 and B4 in Comparative Example 2 were visually assessed. In case of A3, a clear and easy-to-handle solution was observed. In case of B4, a thick slurry was produced. FIGS. 4 and 5 showed pictures that were taken from the respective reaction vessels during the reaction.

The invention claimed is:

1. A process for the production of compounds of formula I

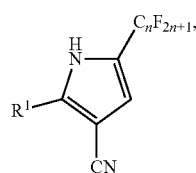

wherein the variables have the following meaning;

$R^1$ phenyl, substituted with none, one, or more, same, or different R11;

R11 F, Cl, Br, I, CN, NO2, OH, C1-C4-alkyl, C1-C4-haloalkyl, C1-C4-alkoxy, C1-C4-haloalkoxy, C1-C4-alkyl-C(O)O, C1-C4-haloalkyl-C(O)O; or two substituents R11 situated at adjacent phenyl ring-atoms together are a group —OCH2O—, —OCF2O, or —CH=CH—CH=CH—, and form, together with the carbon atoms to which they are attached a 5- or 6-membered ring; and n 1, 2, or 3;

comprising a Step A of reacting compounds of formula II

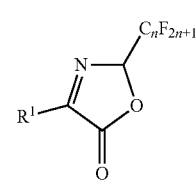

wherein the variables have the same meaning as defined for compounds of formula I;

with 2,3-dihalopropionitrile or 2-haloacrylonitrile in the presence of diisopropylethylamine.

2. The process according to claim 1, wherein the Step A is carried out in a solvent comprising a polar aprotic solvent.

3. The process according to claim 1, wherein compounds of formula I are produced by reaction of compounds of formula II with 2,3-dichloropropionitrile.

4. The process according to claim 1 further comprising a process Step B for the production of compounds of formula III

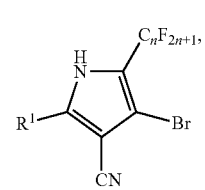

wherein the variables have a meaning as defined for compounds of formula I;

the Step B comprising reacting compounds of formula I

with $Br_2$ in the presence of diisopropylethylamine.

5. The process according to claim 4, wherein Step B is carried out in in a solvent comprising a polar aprotic solvent.

6. The process according to claim 4, wherein Steps A and B are carried out as a one-pot process.

7. The process according to claim 1, wherein $R^1$ is para-chlorophenyl, and n is 1.

8. The process according to claim 4 further comprising a process Step C for the production of compounds of formula IV

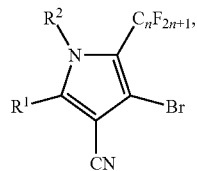

(IV)

wherein the variables $R^1$ and n have a meaning as defined for compounds of formula (I), and
$R^2$ is $C_1$-$C_4$-alkoxymethyl;
the Step C comprising reacting compounds of formula III

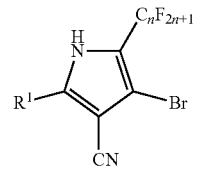

(III)

with di($C_1$-$C_4$-alkoxy)methane and either $POCl_3$, or a mixture comprising $POCl_3$ and DMF (Vilsmeier reagent), in the presence of diisopropylethylamine.

9. The process according to claim 8, wherein $R^1$ is p-chlorophenyl, n is 1, and $R^2$ is $CH_3CH_3OCH_2$.

10. The process according to claim 8, wherein the Step C is carried out in a solvent comprising aliphatic $C_5$-$C_{16}$-hydrocarbons, an aromatic $C_6$-$C_{10}$-hydrocarbons, halogenated aliphatic $C_1$-$C_6$-alkanes, halogenated aromatic $C_6$-$C_{10}$-hydrocarbons, $C_1$-$C_6$-nitriles, DMF, or a mixture thereof.

11. The process according to claim 1, wherein compounds of formula II are produced by reacting compounds of formula V

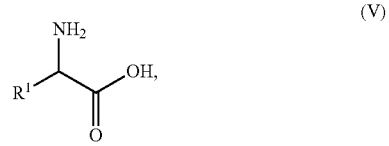

(V)

wherein $R^1$ has a meaning as defined for compounds of formula IV;
with $C_nF_{2n+1}C(O)Cl$ and $PCl_3$.

12. The process according to claim 11, wherein the production of compounds of formula II and the Step A are carried out in a one-pot process.

13. The process according to claim 2, wherein the Step A is carried out in a solvent comprising acetonitrile.

14. The process according to claim 5, wherein the Step B is carried out in in a solvent comprising acetonitrile.

* * * * *